United States Patent [19]
Ewall

[11] Patent Number: 5,607,388
[45] Date of Patent: Mar. 4, 1997

[54] MULTI-PURPOSE WOUND DRESSING

[75] Inventor: Ralph Ewall, Newark, Del.

[73] Assignee: Hercules Incorporated, Wilmington, Del.

[21] Appl. No.: 261,360

[22] Filed: Jun. 16, 1994

[51] Int. Cl.$^6$ .................................................. A61F 13/00
[52] U.S. Cl. ............................ 602/58; 602/92; 604/309
[58] Field of Search .............................. 602/41–43, 47, 602/48, 52, 54, 56, 57, 58, 59; 604/378, 304

[56] References Cited

U.S. PATENT DOCUMENTS

| 3,367,329 | 2/1968 | Dibelius | 602/58 E |
| 3,419,006 | 12/1968 | King. | |
| 3,645,835 | 2/1972 | Hodgson. | |
| 3,664,343 | 5/1972 | Assarsson. | |
| 3,888,247 | 6/1975 | Stenvall | 128/155 |
| 3,972,328 | 8/1976 | Chen. | |
| 3,993,551 | 11/1976 | Assarsson et al.. | |
| 4,094,316 | 6/1978 | Nathanson | 128/156 |
| 4,181,127 | 1/1980 | Linsky et al. | 128/155 |
| 4,231,357 | 11/1980 | Hessner | 128/156 |

(List continued on next page.)

FOREIGN PATENT DOCUMENTS

| 0099758 | 2/1984 | European Pat. Off.. |
| 0106439 | 4/1984 | European Pat. Off.. |
| 0106440 | 4/1984 | European Pat. Off.. |
| 0174803 | 3/1986 | European Pat. Off.. |
| 0190814 | 8/1986 | European Pat. Off.. |
| 0236104 | 8/1987 | European Pat. Off.. |
| 0304536 | 3/1989 | European Pat. Off.. |
| 0410009 | 1/1991 | European Pat. Off.. |
| 0236104 | 3/1987 | Germany. |
| 0304536A2 | 2/1988 | Germany. |
| 0106440 | 6/1983 | United Kingdom. |
| 0099758 | 7/1983 | United Kingdom. |
| 0106439 | 8/1983 | United Kingdom. |
| 8705206 | 9/1987 | WIPO. |

OTHER PUBLICATIONS

Knighton et al., Oxygen Tension Regulates the Expression of Angiogenesis Factor by Macrophages, Science 1983; vol. 211; pp. 1283–1285.

Kaufman et al., The Microclimate Chamber: The Effect of Continuous Topical Admin. of 96% Oxygen . . . ; J. of Trauma, 1983; vol. 23, No. 9; pp. 806–815.

Hunt et al., The Effect of Varying Ambient Oxygen Tensions on Wound Metabolism & Collagen Synthesis; 1972, vol. 135; pp. 561–567.

Balin et al., The Effect of Oxygen Tension on the Growth & Metabolism of W1–38 Cells$^{1,2}$, J. Cell. Physio., 89, pp. 235–249.

Varghese et al., Local Environment of Chronic Wounds Under Synthetic Dressings; J. Arch. Dermatol., vol. 122; Jan. 1986; pp. 51–57.

Niinkikoski et al., J. Surgery, Gynecol. & Obstetc; Dec. 1971; vol. 133; pp. 1003–1007.

Primary Examiner—Randall L. Green
Assistant Examiner—Chalin Smith
Attorney, Agent, or Firm—Martin F. Sloan; Mark Goldberg

[57] ABSTRACT

Liquid and pathogen impermeable island wound dressing which can be adhesively bonded to the skin surrounding a wound is provided with a liquid and gas permeable exudate absorbing pad, and a plurality of sequentially removable liquid and microorganism impermeable, gas and moisture vapor permeable cover sheets disposed adjacent to and covering the pad.

22 Claims, 1 Drawing Sheet

U.S. PATENT DOCUMENTS

| | | | |
|---|---|---|---|
| 4,281,650 | 8/1981 | Spiegelberg . | |
| 4,413,621 | 11/1983 | McCracken et al. . | |
| 4,477,325 | 10/1984 | Osburn . | |
| 4,499,896 | 2/1985 | Heinecke . | |
| 4,538,603 | 9/1985 | Pawelchak et al. . | |
| 4,554,317 | 11/1985 | Behar et al. . | |
| 4,554,371 | 11/1985 | Majoie . | |
| 4,561,435 | 12/1985 | McKnight et al. | 128/156 |
| 4,598,004 | 7/1986 | Heinecke . | |
| 4,600,001 | 7/1986 | Gilman . | |
| 4,638,797 | 1/1987 | Merrill et al. . | |
| 4,641,643 | 2/1987 | Greer | 128/156 |
| 4,645,624 | 2/1987 | Ramm et al. . | |
| 4,649,909 | 3/1987 | Thompson | 128/156 |
| 4,657,006 | 4/1987 | Rawlings et al. . | |
| 4,738,257 | 4/1988 | Meyer et al. . | |
| 4,753,231 | 6/1988 | Lang et al. | 128/156 |
| 4,798,201 | 1/1989 | Rawlings et al. | 128/156 |
| 4,813,942 | 3/1989 | Alvarez | 604/290 |
| 4,875,473 | 10/1989 | Alvarez | 128/155 |
| 4,906,240 | 3/1990 | Reed et al. | 604/307 |
| 4,977,892 | 12/1990 | Ewall | 128/156 |
| 5,056,510 | 10/1991 | Gilman . | |
| 5,060,642 | 10/1991 | Gilman . | |
| 5,086,763 | 2/1992 | Hathman | 602/42 |
| 5,092,323 | 3/1992 | Riedel et al. | 602/54 |
| 5,106,629 | 4/1992 | Cartmell et al. . | |
| 5,139,861 | 8/1992 | Williams et al. | 428/288 |
| 5,145,676 | 9/1992 | Fahey, III et al. | 425/85.1 |
| 5,244,457 | 9/1993 | Karami et al. . | |
| 5,264,218 | 11/1993 | Rogozinski | 424/445 |
| 5,308,313 | 5/1994 | Karami et al. . | |

MULTI-PURPOSE WOUND DRESSING

This invention relates to an island wound dressing having a plurality of cover sheets that are liquid and microorganism impermeable and moisture vapor and gas permeable.

BACKGROUND OF THE INVENTION

Healing of dermal wounds progresses through a number of phases that optimally require different wound environments of oxygen, carbon dioxide and moisture. For all but the least severe wounds, during the initial healing phase, there is a high exudation. Optimally high exudate removal and high oxygen supply are desirable during this healing phase, during which time angiogenesis and internal tissue and skin growth begin. Thereafter exudation decreases and healing progresses, with reepithelization and wound remottling beginning. During this healing phase, still high or even higher oxygen level then during the initial phase is optimal. Less exudate removal is desired to avoid desiccation of the wound. Thereafter, in the final phase of healing, reepithelization is completed, and wound approximation and closure takes place. Exudation decreases and then stops, and the final scar tissue forms, completing the healing process. During this healing phase a higher oxygen, low to dry moisture microenvironment is appropriate.

Since the wound healing phases have different optimal healing microenvironments, optimally different types of dressings should be used during the individual healing phases. These dressings should have different permeability characteristics designed to provide the appropriate gas and moisture microenvironments for each phase. In practice, different types of wound dressings, which provide appropriate microenvironments during the individual healing phases, are seldom used. The number of different types of wound dressings required is too great for practical inventorying.

Not only is there a need for a single wound dressing that can provide appropriate microenvironments during more than a single phase of wound healing, but there also is a need for a single dressing that can provide the appropriate wound microenvironment for different types of wounds. For example, it would be useful to have a single dressing that can be used for both high and low exudative wounds.

Many wound dressings in common use are occlusive, permitting little or no water vapor or gas transmission. Many others do permit water vapor and gas transmission, but are not capable of providing more than a single wound microenvironment. See U.S. Pat. Nos. 4,561,435; 4,753,231; 4,798, 201; 4,813,942; 4,906,240; and EPs. 0106439; 0106440; 0174803 and 0410009.

U.S. Pat. No. 4,875,473 describes a dressing that is capable of modifying the wound environment. However, the dressing has a substantially occlusive outer cover sheet impermeable to oxygen during its initial usage. Thereafter it is converted, by removal of the impermeable outer sheet, to an oxygen permeable dressing, giving only a single aerobic wound environment phase. No concept of varying oxygen levels is disclosed.

EP 0099758 discloses a dressing capable of low initial moisture removal, convertible to high moisture vapor removal. This reference contains no disclosure concerning oxygen level control during the healing phase.

SUMMARY OF THE INVENTION

The present invention relates to a liquid and microorganism impermeable wound dressing, the moisture and gas permeabilities of which can be changed during use without removal of the dressing from the patient. The dressing comprises an exudate absorbent pad to be in liquid conducting contact with the wound, and a plurality of cover sheets on the outer side of the pad that are of predetermined combined permeability to moisture vapor and gas, and thereby control the microenvironment of the wound. The outer cover sheets are removable from the dressing, imparting to the dressing the permeability of the remaining cover sheets. Thus, the dressing can be used through a plurality of wound healing conditions, providing different microenvironments to the wound during healing, without removal of the entire dressing from the patient. Also, the dressing can be adapted before use for application to a plurality of wound types, minimizing inventory requirements.

DETAILED DESCRIPTION OF THE INVENTION

The present invention dressing is an island dressing that is liquid and microorganism impermeable, and comprises: (a) a liquid and gas permeable exudate absorbing pad having a wound facing inner surface that in use is in liquid conducting contact with the wound, and an opposing outer surface; (b) a plurality of liquid and microorganism impermeable, gas and moisture vapor permeable cover sheets disposed parallel to, adjacent to, and covering the outer surface of the pad; (c) means for adhesively bonding the pad and cover sheets to the skin; and (d) means for sequentially removing outer cover sheets from the outer side of the dressing.

Figure 1:
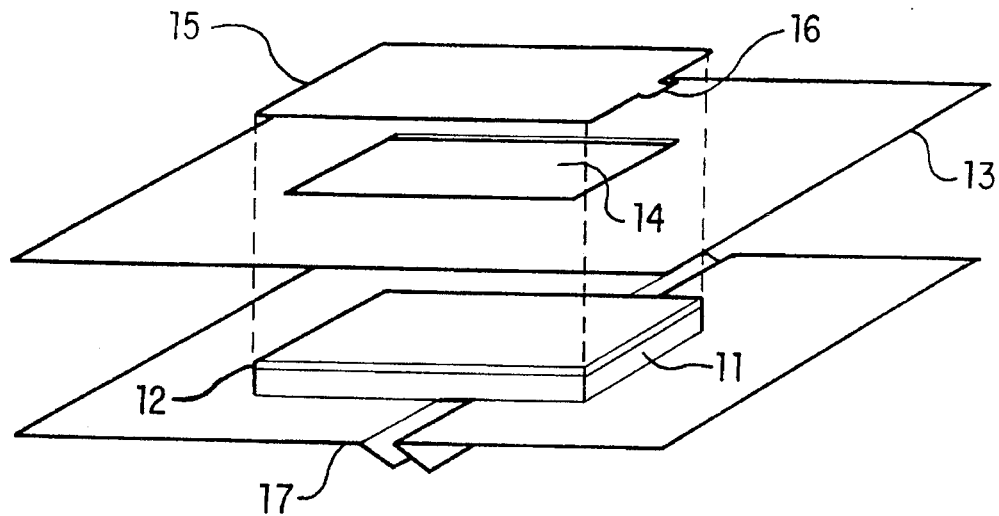
Figure 2:
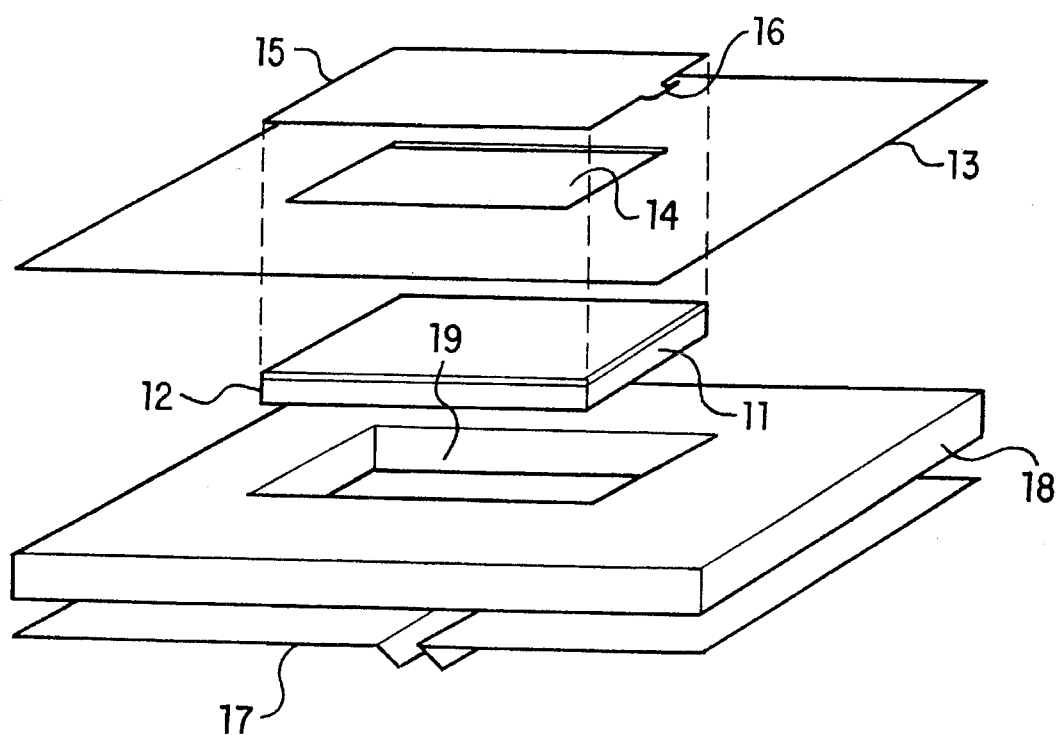

The island wound dressing of the present invention may take any convenient form or shape so long as it meets the above requirements. In the drawings, FIG. 1, shows a preferred dressing of the present invention. FIG. 2 shows another preferred dressing that has a fenestrated base layer to minimize the need for complete dressing changes.

Referring to FIG. 1, on the outer side of absorbent pad 11 is an inner cover sheet 12 adjacent to, parallel to, and covering the outer surface of pad 11. Preferably, the pad and inner cover sheet are heat bonded together into a pad/inner cover sheet laminate. Attachment layer 13 has a fenestration 14 that fits over inner cover sheet 12 and pad 11. The fenestration 14 is smaller than inner cover sheet 12. The attachment layer 13 has a pressure sensitive adhesive (PSA) on its inner side and adhesively bonds inner cover sheet 12 and pad 11 to the healthy skin periphery of the wound. Outer cover sheet 15, with tab 16 for easy removal, is larger in area than and fits over fenestration 14 adhesively bonded to attachment layer 13. Release liner 17, removably bonded to pad 11 and attachment 13, is for ease of handling prior to use.

A wound dressing comprising more than the two cover sheets shown in the figures, can be constructed by simply placing another fenestrated attachment layer on the outside of cover sheet 15 adhesively bonded to attachment layer 13, and adhesively attaching another outer cover sheet at its periphery over the fenestration of the second attachment layer.

The wound dressing may also have a base layer. The use of a base layer is particularly desirable when a large number of dressing changes will be required during wound healing. The base layer may remain on the patient for up to 10 or more days. During this period the pad and cover sheets may be changed without trauma to the wound that could be caused by removal of the entire dressing from the wound peripheral skin.

As shown in FIG. 2, base layer 18 has a fenestrated area 19 larger than the wound, into which the pad 11 fits snugly positioned to be in exudate conducting contact with the wound. The base layer 18 adhesively attaches the dressing to the undamaged skin periphery of the wound. The top of base layer 18 and fenestrated attachment layer 13 are adhesively bonded together, holding pad 11 and inner cover sheet 12 in base layer fenestration 19. Outer cover sheet 15 with tab 16 is adhesively bonded to the outer side of the periphery of fenestration 14 in attachment layer 13. Release liner 17 covers the skin side of the dressing for ease of handling before use. Attachment layer 13 may not be needed if inner cover sheet 12 is larger in area than pad 11 and is bonded directly to the fenestration periphery of base layer 18.

In use, the pad functions to absorb exudate as it forms in the wound, preventing exudate pooling while maintaining the wound moist. The pad delivers the exudate to the inner cover sheet, which passes the aqueous portion through as moisture vapor, to the outside cover sheets that remain on the dressing, and on to the outside air.

The absorbent pad contains one or more layers of absorbent material in adequate quantity. Many non-toxic conventional known absorbent materials are readily available. Preferred pad materials are gauze, non-woven sheet materials, cellulosic pulp, synthetic pulp, cottony rayon and absorbent sponges. The pad size and shape will vary with the size and shape of the wound. It should be large enough to cover the wound, and preferably is capable of absorbing at least about 2 to about 20 cc/g of pad of exudate. Optionally the pad can contain known absorbent particles and medicaments, such as antibiotics and wound healing stimulants.

Preferably the wound-facing surface of the pad is treated with a layer of material that renders the pad non-adhering to the wound without significantly interfering with it's absorbing capability. Suitable treatments including lining the wound-facing inner side of the pad with a highly liquid-permeable non-stick layer such as a polymeric net, mesh or perforated film. "Delnet" P530 apertured polyethylene mesh (Applied Extrusion Technology, Inc.) is excellent. Alternatively, the pad can be coated with a hydrogel material or other non-stick material that does not interfere significantly with exudate absorption.

The term "gas" as used herein, refers to oxygen and carbon dioxide. In practice, normally only the oxygen permeability of a cover sheet material is measured, because carbon dioxide permeabilities of cover sheets are much less critical than oxygen permeabilities. From a practical standpoint, if a cover sheet material has adequate oxygen permeability it also has adequate carbon dioxide permeability.

The inner cover sheet is parallel to, adjacent to, and substantially covers the outer side of the pad. The inner cover sheet and pad may be heat or adhesively bonded thereto. If the dressing has a base layer, the pad also is adhesively bonded to the periphery of the base layer fenestration, either directly or by an attachment layer. The cover sheets are the dressing component essential for controlling the wound microenvironment liquid and gas levels. The cover sheets are liquid and microorganism impermeable and permeable to moisture vapor and gas.

The gas and moisture vapor permeabilities of the dressing change, normally increase, as each successive outer cover sheet is removed from the outer side of the dressing. Each cover sheet is selected so that the overall dressing, that is the combination of cover sheets, has the desired permeabilities for the healing phase during which the dressing will be used initially. Then removal of each successive outer cover sheet will change the moisture and gas permeabilities.

For example, it may be desirable to have during initial use, a dressing with moderate oxygen permeability and low moisture vapor permeability, and subsequently higher oxygen and moisture permeabilities. This can be achieved by using a two cover sheet dressing, the inner cover sheet being selected to have the ultimate use high oxygen and moisture vapor permeabilities, and the outer cover sheet being selected to have oxygen and moisture vapor permeabilities that, in conjunction with the inner cover sheet, will give the initially desired levels of moderate oxygen permeability and low moisture vapor permeability. The dressing with the two cover sheets is applied to the dressing. At the start of the second period of use of the dressing, the outer cover sheet is removed from the dressing, leaving only the inner cover sheet, which thereafter dictates the permeabilities of the dressing.

This same dressing may be used in the initial healing of a wound requiring both high moisture vapor and high oxygen permeabilities, by simply peeling off (by a tab) and discarding before use the outer cover sheet, giving a dressing with the desired high inner cover sheet permeabilities. Thus the dressing has the versatility of being used on wounds requiring either of two distinct microenvironments.

Because the oxygen requirement is high throughout the healing of many wounds, the preferred present invention dressings have throughout their usage period, where a plurality or only the inner cover sheet is on the dressing, oxygen permeabilities of at least about 10,000 cc/m²/day/atm measured at 25° C. and 50% relative humidity; and MVTR's of at least about 300 g/m²/day at ambient pressure, 25° C. and 50% R.R., and most preferably in the range of at least about 300 g/m²/day to about 5000 g/m²/day.

The permeability of a dressing having two or more cover sheets is conventionally calculated by the formula:

$$\frac{1}{\text{Permeability}} = \frac{1}{K_1} + \frac{1}{K_2} \text{ etc.} \quad (1)$$

where Permeability is the dressing permeability, and $K_1$, $K_2$ etc. are the permeabilities of the individual cover sheets.

Gas permeances and moisture vapor transmission rate (MVTR) of a number of useful cover sheet materials are listed in Table 1. Using the permeabilities (Permeance divided by mils thickness) of the films of Table 1 in formula (1), one can select combinations of films having desired permeabilities.

TABLE 1

| FILM | MVTR | $O_2$ PERM/$CO_2$ PERM | | THICKNESS MILS |
|---|---|---|---|---|
| Microporous polyolefin PM-3 (Consolidated Thermoplastics Corp. | 3800 | 21,700,000 (a) | 21,700,000 (a) | 0.8 |
| Microporous polyolefin | 950 | 8,640,000 (a) | 8,640,000 (a) | 4.8 |

TABLE 1-continued

| FILM | MVTR | O$_2$PERM/CO$_2$PERM | | THICKNESS MILS |
|---|---|---|---|---|
| X-25813-24-1 (Hercules Incorporated) Microporous polyolefin | 360 | 294,500 | 1,473,000 | 4.2 |
| X-27448-44-4 (Hercules Incorporated) Microporous polyolefin | 150 | 357,000 | 357,000 | 7.3 |
| X-28244-13-4 (Hercules Incorporated) Microporous polyolefin | 140 | 138,000 | 138,000 | 7.2 |
| X-28244-13-3 (Hercules Incorporated) Silicone (Surgitec Corp.) | — | >100,000 | 646,500 | 1.3 |
| Styrenebutadienestyrene (Consolidated Thermoplastics Corp.) | ~200 | 64,000 | 214,000 | 1.0 |
| Polyether block imide MF-827 (Bertek Corp.) | 2000 | 49,800 | — | 1.0 |
| Copolyester MF-3548 (Bertek Corp.) | 2175 | 33,800 | >20,000,000 | 1.5 |
| Polyurethane 946B (PCF-MED Corp.) | 1400 | 20,600 | 167,500 | 1.5 |
| Polyetherpolyurethane KM-1391-02 (Semex Corp.) | 960 | 14,675 | 84,200 | 2.7 |
| Copolyester KM-1353-06 (Semex Corp.) | 870 | 13,000 | 126,500 | 3.0 |
| Copolyester MED 5002 (Fasson Corp.) | 390 | 10,418 | — | 2.0 |
| Copolyester MF-325 (Bertek Corp.) | 300 | 9,600 | 111,500 | 0.7 |
| Low Density Polyethylene (USI Corp.) | ~30 | 2,800 | 12,000 | 3.0 |
| Polyesterpolyurethane KH-1393-00 (Semex Corp.) | 330 | 1,270 | 10,200 | 4.0 |
| Cellophane P4T (Flexel Corp.) | 2300 | 17 | >40 | 1.5 |

(a) measured by an experimental method for high permeable films.
Units for MVTR are g/sq.m./24 hrs. at ambient conditions of pressure, 25 deg. C. and 50% R.H.; and for O$_2$ and CO$_2$ Perm(eance) are cc/sq.m./24 hrs/atm, at 25 deg. C. and 50% R.H. Units of thickness are mils.

If used, the fenestrated base layer (FIG. 2) may be an integral part of the dressing. Alternatively it may be a separate unit that is used in conjunction with the dressing. The base layer strongly adheres to the wound periphery skin so that it can remain in place throughout an extended time period. The base layer material can itself be sufficiently adhesive, or a barrier pressure sensitive adhesive layer may be applied to the skin side of the base layer. The adhesiveness must be sufficient to hold the base layer on the skin when pulling outer cover sheets off the dressing. Thus the inner cover sheet and pad, adhesively bonded to the base layer, can be readily removed from the dressing. This permits cleaning and medicating without trauma to the wound-periphery skin.

The base layer can be any flexible, comfortable film material that is a barrier to liquids, gas and microorganisms. By "barrier" is meant that the base layer will not permit passage therethrough of significant amounts of liquids, gas or microorganisms. Preferably it is adequately moisture absorbent to take up perspiration, thereby maintaining good adhesive bonding to the skin. Excellent base layers can be made of commercially available sheet material having the appropriate properties described above, such as rubber-based adhesive wafers that can be window cut for the fenestration that accommodates the pad. Ideal materials are "DUODERM" compounded rubber sheet material, a product of Bristol-Myers-Squib Corp.; and "Veriseal" A15, A15 Mod. and A 52 adhesive films, products of Veriseal Corp.

The fenestrated attachment layer that adhesively bonds the dressing to the skin (FIG. 1), or onto the base layer (FIG. 2), can be made of conventional film of polyester, polyurethanes, copolyesters, polyether block imides, polyvinyl chloride, polyethylene, polypropylene, polybutane, latex rubbers and combinations of foam and film. A preferred film for use as the fenestrated attachment layer film in 20LF Type II reinforced polyurethane film from Gila River Corp., coated with a barrier PSA.

For ease in handling, preferably a conventional release liner is used to cover the adhesive skin side of the dressing (with or without a base layer), during handling before application. Silicone coated release liner W89SP/P (a product of Mead Paper Products, West Chicago, Ill.) in an overtape or plowfold configuration is an excellent release liner.

The following Examples illustrate the preferred embodiments of the present invention.

EXAMPLE 1

An island wound dressing of the type shown in FIG. 1 is made, having a low MVTR and moderate oxygen permeability when both the inner and outer cover sheets are on the dressing. When the outer cover sheet is stripped off, the dressing then has high MVTR and high oxygen permeability.

This dressing has an absorbent pad 4"×4"×¼" thick made of "Synpulp" 232.100 absorbent pad material, having an absorbency of over 10 cc/g of pad. "Synpulp" 232.100 is fluffed wood pulp intimately blended with "Pulpex" polypropylene/polyethylene fibrous material treated with the wetting agent, made by Hercules Incorporated. The inner cover sheet is 4"×4" of Bertek Corp. MF 3548 copolyester film 1.0 mils thick. The MVTR of this sheet is 2175 g/m$^2$/day and the oxygen permeability 33,800 cc/m$^2$/day/atm, each at 25° C. and 50% R.H. The inner cover sheet and the outer side of the pad are thermally bonded together into a laminate.

The skin attachment layer is made from polyurethane adhesive coated film 20 LF Type II made by Gila River Corp., cut to a 5"×5" sheet having a fenestration of 3"×3" centered therein. The adhesive wound-side of the attachment layer is bonded to the periphery of the inner cover sheet/pad laminate so that the inner cover sheet is centered above the fenestration.

An outer cover sheet 4"×4" and 1 mil thick cut from KM-1393-00 polyesterpolyurethane film made by Semex Corp., is PSA bonded at its periphery to the outer side of the attachment layer centered over the fenestration. This outer cover sheet has a tab for easy removal from the dressing. The outer cover sheet has an MVTR of 330 g/m$^2$/day and an oxygen permeability of 1270 cc/m$^2$/day/atm., each at 25° C. and 50% R.H.

For ease of handling prior to application to a patient, a plow-cut release liner 5"×5" of W89SP (Mead Paper Products) silicone coated paper is placed on the wound-side of the dressing.

The dressing, with both cover sheets in place has an MVTR of about 320 g/m$^2$/day and an oxygen permeability of about 1224 cc/m$^2$/day/atm, both at 25° C. and 50% R.H. It is pathogen and liquid impermeable, and permeable to gas (oxygen and carbon dioxide) and moisture vapor from exudate absorbed by the pad.

The dressing with both cover sheets in place has low MVTR and moderate gas permeability and so is suited for use on a low exudate partial thickness dermal wound. With the outer cover sheet removed, this dressing has high MVTR and high oxygen permeability and is suited for use on a high exudate fresh full thickness dermal wound.

EXAMPLE 2

The procedure of Example 1 is followed to prepare a FIG. 1 type wound dressing, except that a non-adhering layer of "Delnet" P530 mesh is bonded onto the wound-side of the pad.

This wound dressing has the same uses as the dressing of Example I, but has the added feature of protection against the dressing adhering to the wound.

EXAMPLE 3

To prepare a FIG. 2 type wound dressing, the procedure of Example 1 is followed except that a fenestrated base layer is placed on the wound-side of the dressing. The base layer is cut from ¼" thick "Veriseal" 15 rubber based adhesive sheet material, cut to a size of 5"×5" with a centered fenestration 4"×4". The inner cover sheet/pad laminate fits snugly into the fenestration in the base layer so that the pad will be in liquid conducting contact with the wound. The attachment layer is PSA bonded to the outer side of the base layer. The silicone coated release layer is placed on the wound-side of the dressing for ease of handling prior to usage.

This dressing is suitable for the same uses as the Example 1 dressing. In use the base layer can remain on the patient for 10 days or more, while the remainder of the dressing is changed several times without trauma to the wound.

EXAMPLE 4

Following the procedures of Example 1 wound dressing having Table 1 cover sheets are prepared. Table 2 lists the inner and outer cover sheet permeabilities and the approximate permeabilities of the dressings as prepared and with the outer cover sheets removed.

TABLE 2

(Example 4)

PERMEABILITIES

| SAMPLE | | Inner Sheet | Outer Sheet | Dressing | With Outer Sheet Removal |
|---|---|---|---|---|---|
| | | KM-1353-06 | MF-325 | | |
| 4 | $O_2$ | 13,000 | 9600 | 5,520 | 13,000 |
| | MVTR | 870 | 300 | 300 | 870 |
| | | MF-827 | MED 5002 | | |
| 5 | $O_2$ | 49,800 | 10,418 | 8616 | 49,800 |
| | MVTR | 2,000 | 390 | 3900 | 2000 |
| | | MF-3548 | KM-1391-02 | | |
| 6 | $O_2$ | 33,800 | 14,675 | 10,230 | 33,800 |
| | MVTR | 2,175 | 960 | 960 | 2,175 |
| | | MF-827 | 946B | | |
| 7 | $O_2$ | 49,800 | 20,600 | 14,570 | 49,800 |
| | MVTR | 2,000 | 1,400 | 1,400 | 2,000 |
| | | X44-4 | MF-827 | | |
| 8 | $O_2$ | 294,500 | 49,800 | 42,600 | 294,500 |
| | MVTR | 360 | 2,000 | 360 | 360 |

Units of $O_2$ permeability are cc/sq.m/day/atm; and MVTR g/sq.m/day at ambient pressure; each at 25° C. and 50% R.H.

What is claimed:

1. A liquid and pathogen impermeable island wound dressing comprising:
    (a) a liquid and gas permeable exudate absorbing pad including a wound facing inner surface and an opposing outer surface;
    (b) a plurality of liquid and microorganism impermeable, gas and moisture vapor permeable cover sheets disposed adjacent to and covering the opposing outer surface of said pad;
    (c) means for adhesively bonding said pad and said plurality of cover sheets to skin surrounding a wound;

(d) said plurality of cover sheets being constructed and arranged to be sequentially removable; and (e) said plurality of cover sheets providing an oxygen permeability of at least 10,000 cc/m$^2$/day/atm.

2. The dressing according to claim 1, wherein said pad comprises a material selected from the group consisting of gauze, non-woven sheet materials, cellulosic pulp, synthetic pulp, cotton, rayon, sponges and foam.

3. The dressing according to claim 1, further including a non-adhering layer on the wound-facing surface of said pad, said non-adhering layer not significantly interfering with exudate absorbing capability of said pad.

4. The dressing according to claim 1, wherein said plurality of cover sheets comprise an outermost cover sheet including a surface area, and further comprising an attachment layer including a fenestration over at least a part of the surface area of the outermost cover sheet and said pad.

5. The dressing according to claim 1, comprising an adhesively bonded release liner covering said wound facing inner side of said pad.

6. The dressing according to claim 1, wherein at least one of said plurality of cover sheets includes a tab to assist sequential removal.

7. The dressing according to claim 1, wherein said plurality of cover sheets are parallel to said pad.

8. The dressing according to claim 1, further comprising a liquid, gas and microorganism barrier base layer that is fenestrated to surround and accommodate said pad, said layer being adhesively bondable to the skin, and said pad is positioned to be in exudate conducting contact with the wound.

9. The dressing according to claim 8, comprising an adhesively bonded release liner covering said wound facing inner side of said pad.

10. A liquid and pathogen impermeable island wound dressing comprising:

(a) a liquid and gas permeable exudate absorbing pad including a wound facing inner surface and an opposing outer surface;

(b) a plurality of liquid and microorganism impermeable, gas and moisture vapor permeable cover sheets disposed adjacent to and covering the opposing outer surface of said pad;

(c) means for adhesively bonding said pad and said plurality of cover sheets to skin surrounding a wound;

(d) said plurality of cover sheets being constructed and arranged to be sequentially removable; and (e) said plurality of cover sheets providing a moisture vapor permeability rate of at least 300 g/m$^2$/day.

11. The dressing according to claim 10, wherein at least one of said plurality of cover sheets includes a tab to assist sequential removal.

12. The dressing according to claim 10, wherein said plurality of cover sheets are parallel to said pad.

13. The dressing according to claim 10, further comprising a liquid, gas and microorganism barrier base layer that is fenestrated to surround and accommodate said pad, said layer being adhesively bondable to the skin, and said pad is positioned to be in exudate conducting contact with the wound.

14. The dressing according to claim 10, wherein said plurality of cover sheets provide an oxygen permeability of at least 10,000 cc/m$^2$/day/atm.

15. The dressing according to claim 10, wherein said plurality of cover sheets provide a moisture vapor permeability rate of about 300 to 5,000 g/m$^2$/day.

16. A liquid and pathogen impermeable island wound dressing comprising:

(a) a liquid and gas permeable exudate absorbing pad including a wound facing inner surface and an opposing outer surface;

(b) a plurality of liquid and microorganism impermeable, gas and moisture vapor permeable cover sheets disposed adjacent to and covering the opposing outer surface of said pad;

(c) means for adhesively bonding said pad and said plurality of cover sheets to skin surrounding a wound;

(d) said plurality of cover sheets being constructed and arranged to be sequentially removable; and (e) said pad comprising a liquid absorbing capacity of about to about 20 cc/g of pad.

17. The dressing according to claim 16, wherein at least one of said plurality of cover sheets includes a tab to assist sequential removal.

18. The dressing according to claim 16, wherein said plurality of cover sheets are parallel to said pad.

19. The dressing according to claim 16, further comprising a liquid, gas and microorganism barrier base layer that is fenestrated to surround and accommodate said pad, said layer being adhesively bondable to the skin, and said pad is positioned to be in exudate conducting contact with the wound.

20. The dressing according to claim 16, wherein said plurality of cover sheets provide a moisture vapor permeability rate of at least about 300 g/m$^2$/day.

21. The dressing according to claim 16, wherein said plurality of cover sheets provide an oxygen permeability of at least 10,000 cc/m$^2$/day/atm.

22. The dressing according to claim 21, wherein said plurality of cover sheets provide a moisture vapor permeability rate of at least about 300 g/m$^2$/day.

\* \* \* \* \*